(12) United States Patent
Kusleika (10) Patent No.: US 8,579,958 B2
(45) Date of Patent: *Nov. 12, 2013

(54) EVERTING STENT AND STENT DELIVERY SYSTEM

(75) Inventor: Richard S. Kusleika, Eden Prairie, MN (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/614,035

(22) Filed: Sep. 13, 2012

(65) Prior Publication Data

US 2013/0066414 A1 Mar. 14, 2013

Related U.S. Application Data (60) Continuation of application No. 12/477,613, filed on Jun. 3, 2009, now Pat. No. 8,317,850, which is a division of application No. 11/035,671, filed on Jan. 14, 2005, now abandoned, which is a continuation of application No. 10/096,628, filed on Mar. 12, 2002, now Pat. No. 6,866,679.

(51) Int. Cl.
*A61F 2/82* (2013.01)

(52) U.S. Cl.
USPC .......................... 623/1.12; 623/903; 623/1.2

(58) Field of Classification Search
USPC ......... 623/1.11–1.13, 903, 1.2; 606/108, 194, 606/198
See application file for complete search history.

(56) References Cited

U.S. PATENT DOCUMENTS

| | | |
|---|---|---|
| 4,294,340 A | 10/1981 | Kunze |
| 4,655,771 A | 4/1987 | Wallsten |
| 4,723,936 A | 2/1988 | Buchbinder et al. |
| 4,950,214 A | 8/1990 | Botterill |
| 4,990,151 A | 2/1991 | Wallsten |
| 5,445,646 A | 8/1995 | Euteneuer et al. |
| 5,571,135 A | 11/1996 | Fraser et al. |
| 5,636,641 A | 6/1997 | Fariabi |
| 5,702,418 A | 12/1997 | Ravenscroft |
| 5,824,041 A | 10/1998 | Lenker et al. |
| 5,890,573 A | 4/1999 | Kwoka |
| 5,935,161 A | 8/1999 | Robinson et al. |
| 5,968,053 A | 10/1999 | Revelas |

(Continued)

FOREIGN PATENT DOCUMENTS

| | | |
|---|---|---|
| DE | 3815225 C2 | 7/1990 |
| DE | 69019929 T2 | 12/1995 |

(Continued)

OTHER PUBLICATIONS

U.S. Appl. No. 13/453,047, filed Apr. 23, 2012.

(Continued)

*Primary Examiner* — Elizabeth Houston (74) *Attorney, Agent, or Firm* — Mark J. Kertz, Esq.

(57) ABSTRACT

A stent delivery assembly is provided that includes a microcatheter, a delivery tube, a stent, and an elongate release member. The stent can have a first end that is (i) disposed within a delivery tube lumen and (ii) constrained by the delivery tube from radially expanding beyond a delivery tube lumen diameter. The stent can have a second end that is (i) disposed outside of a delivery tube distal end and (ii) substantially radially unconstrained by the delivery tube to expand beyond the delivery tube lumen diameter. The elongate release member can be moveable between first and second positions to engage or release the stent.

26 Claims, 2 Drawing Sheets

(56) References Cited

U.S. PATENT DOCUMENTS

| | | |
|---|---|---|
| 6,003,395 A | 12/1999 | Rogg et al. |
| 6,077,295 A | 6/2000 | Limon et al. |
| 6,077,297 A | 6/2000 | Robinson et al. |
| 6,126,685 A | 10/2000 | Lenker et al. |
| 6,149,680 A | 11/2000 | Shelso et al. |
| 6,193,739 B1 | 2/2001 | Chevillon et al. |
| 6,251,132 B1 | 6/2001 | Ravenscroft et al. |
| 6,264,683 B1 | 7/2001 | Stack et al. |
| 6,350,278 B1 | 2/2002 | Lenker et al. |
| 6,383,171 B1 | 5/2002 | Gifford et al. |
| 6,395,017 B1 | 5/2002 | Dwyer et al. |
| 6,419,693 B1 | 7/2002 | Fariabi |
| 6,428,552 B1 | 8/2002 | Sparks |
| 6,443,971 B1 | 9/2002 | Boylan et al. |
| 6,468,298 B1 | 10/2002 | Pelton |
| 6,517,547 B1 | 2/2003 | Feeser et al. |
| 6,562,063 B1 | 5/2003 | Euteneuer et al. |
| 6,576,006 B2 | 6/2003 | Limon et al. |
| 6,578,693 B2 | 6/2003 | Mayr |
| 6,602,271 B2 | 8/2003 | Adams et al. |
| 6,699,274 B2 | 3/2004 | Stinson |
| 6,706,055 B2 | 3/2004 | Douk et al. |
| 6,715,375 B2 | 4/2004 | Nestler |
| 6,764,504 B2 | 7/2004 | Wang et al. |
| 6,808,529 B2 | 10/2004 | Fulkerson |
| 6,815,325 B2 | 11/2004 | Ishii |
| 6,830,575 B2 | 12/2004 | Stenzel et al. |
| 6,843,802 B1 | 1/2005 | Villalobos et al. |
| 6,866,679 B2 | 3/2005 | Kusleika |
| 6,932,837 B2 | 8/2005 | Amplatz et al. |
| 6,960,227 B2 | 11/2005 | Jones et al. |
| 6,989,024 B2 | 1/2006 | Hebert et al. |
| 7,001,422 B2 | 2/2006 | Escamilla et al. |
| 7,011,675 B2 | 3/2006 | Hemerick et al. |
| 7,074,236 B2 | 7/2006 | Rabkin et al. |
| 7,147,656 B2 | 12/2006 | Andreas et al. |
| 7,306,624 B2 | 12/2007 | Yodfat et al. |
| 7,357,812 B2 | 4/2008 | Andreas et al. |
| 7,371,248 B2 | 5/2008 | Dapolito et al. |
| 7,427,288 B2 | 9/2008 | Sater |
| 7,473,271 B2 | 1/2009 | Gunderson |
| 7,473,272 B2 | 1/2009 | Pryor |
| 7,572,290 B2 | 8/2009 | Yodfat et al. |
| 7,651,520 B2 | 1/2010 | Fischell et al. |
| 7,655,031 B2 | 2/2010 | Tenne et al. |
| 7,691,138 B2 | 4/2010 | Stenzel et al. |
| 7,867,267 B2 | 1/2011 | Sullivan et al. |
| 7,942,925 B2 | 5/2011 | Yodfat et al. |
| 7,955,370 B2 | 6/2011 | Gunderson |
| 7,993,385 B2 | 8/2011 | Levine et al. |
| 8,025,692 B2 | 9/2011 | Feeser |
| 8,034,095 B2 | 10/2011 | Randolph et al. |
| 8,042,720 B2 | 10/2011 | Shifrin et al. |
| 8,066,754 B2 | 11/2011 | Malewicz |
| 8,092,508 B2 | 1/2012 | Leynov et al. |
| 8,133,266 B2 | 3/2012 | Thomas et al. |
| 8,147,534 B2 | 4/2012 | Berez et al. |
| 8,317,850 B2 | 11/2012 | Kusleika |
| 2001/0047919 A1 | 12/2001 | Mayr |
| 2002/0194941 A1 | 12/2002 | Hulsebusch et al. |
| 2004/0024416 A1 | 2/2004 | Yodfat et al. |
| 2005/0125051 A1 | 6/2005 | Eidenschink et al. |
| 2005/0143773 A1 | 6/2005 | Abrams et al. |
| 2006/0058865 A1 | 3/2006 | Case et al. |
| 2006/0212042 A1 | 9/2006 | Lamport et al. |
| 2007/0117645 A1 | 5/2007 | Nakashima |
| 2007/0203563 A1 | 8/2007 | Hebert et al. |
| 2007/0255388 A1 | 11/2007 | Rudakov et al. |
| 2008/0027528 A1 | 1/2008 | Jagger et al. |
| 2008/0033528 A1 | 2/2008 | Satasiya et al. |
| 2008/0140180 A1 | 6/2008 | Dolan et al. |
| 2008/0147162 A1 | 6/2008 | Andreas et al. |
| 2008/0243225 A1 | 10/2008 | Satasiya et al. |
| 2008/0255653 A1 | 10/2008 | Schkolnik |
| 2008/0300667 A1 | 12/2008 | Hebert et al. |
| 2009/0143849 A1 | 6/2009 | Ozawa et al. |
| 2009/0264985 A1 | 10/2009 | Bruszewski |
| 2009/0318947 A1 | 12/2009 | Garcia et al. |
| 2010/0069852 A1 | 3/2010 | Kelley |
| 2010/0087913 A1 | 4/2010 | Rabkin et al. |
| 2010/0094394 A1 | 4/2010 | Beach et al. |
| 2010/0204770 A1 | 8/2010 | Mas et al. |
| 2010/0262157 A1 | 10/2010 | Silver et al. |
| 2010/0274270 A1 | 10/2010 | Patel et al. |
| 2010/0298931 A1 | 11/2010 | Quadri et al. |
| 2011/0022157 A1 | 1/2011 | Essinger et al. |
| 2011/0029065 A1 | 2/2011 | Wood et al. |
| 2011/0034987 A1 | 2/2011 | Kennedy |
| 2011/0106235 A1 | 5/2011 | Haverkost et al. |
| 2011/0178588 A1 | 7/2011 | Haselby |
| 2011/0190862 A1 | 8/2011 | Bashiri et al. |
| 2011/0319904 A1 | 12/2011 | Hollett et al. |
| 2012/0029607 A1 | 2/2012 | McHugo et al. |
| 2012/0035700 A1 | 2/2012 | Leanna et al. |
| 2012/0053681 A1 | 3/2012 | Alkhatib et al. |
| 2012/0059449 A1 | 3/2012 | Dorn et al. |

FOREIGN PATENT DOCUMENTS

| | | |
|---|---|---|
| DE | 19650039 A1 | 6/1997 |
| DE | 10033484 A1 | 1/2002 |
| DE | 10033482 B4 | 5/2004 |
| DE | 10129795 B4 | 9/2006 |
| EP | 2 078 512 | 7/2009 |
| WO | WO-96/01591 | 1/1996 |
| WO | WO-01/49212 A1 | 7/2001 |
| WO | WO-01/89619 A8 | 2/2002 |
| WO | WO-2007/117645 A2 | 10/2007 |
| WO | WO-2010/127838 A2 | 11/2010 |
| WO | WO-2011/076408 | 6/2011 |
| WO | WO-2011/095966 | 8/2011 |
| WO | WO-2012/040240 | 3/2012 |

OTHER PUBLICATIONS

U.S. Appl. No. 13/483,047, filed Apr. 23, 2012.
U.S. Appl. No. 13/553,855, filed Jul. 20, 2012.
U.S. Appl. No. 13/614,349, filed Sep. 13, 2012.
U.S. Appl. No. 13/692,021, filed Dec. 3, 2012.
U.S. Appl. No. 13/664,547, filed Oct. 31, 2012.

EVERTING STENT AND STENT DELIVERY SYSTEM

CROSS REFERENCE TO RELATED APPLICATIONS

This application is a continuation of U.S. application Ser. No. 12/477,613, filed Jun. 3, 2009 now U.S. Pat. No. 8,317,850, which is a divisional of U.S. application Ser. No. 11/035,671, filed Jan. 14, 2005, now abandoned, which is a continuation of U.S. application Ser. No. 10/096,628, filed Mar. 12, 2002, now U.S. Pat. No. 6,866,679, the entire contents thereof are incorporated herein by reference in their entirety.

FIELD OF THE INVENTION

The present invention relates generally to medical devices. More specifically, the present invention relates to stents. The stents may find particular use in intravascular procedures in general, and in cardiovascular procedures in particular, as well as other areas.

BACKGROUND OF THE INVENTION

Stents are well known to those skilled in the biomedical arts. In particular, stents are commonly used in cardiovascular applications. Stents have gained increasing acceptance, particularly when used in conjunction with minimally invasive procedures such as angioplasty. Blockages of the coronary arteries may result from various causes, including plaque build-up, and stenosed or thrombosed vessel regions. The vessel regions thus partially occluded can cause angina and, when totally occluded, myocardial infarction, and even death. Minimally invasive procedures such as balloon angioplasty have been used to dilate such blocked vessel regions, thereby at least partially restoring patent vessel lumens.

In a significant percentage of cases, a stenosed, then dilated vessel region may narrow after treatment over a period ranging from days to months. This re-narrowing or restenosis, limits the efficacy of the angioplasty procedures, may require further angioplasty, or can lead to myocardial infarction and even death.

Cerebral blockages are typically caused by a thrombus. The thrombus can form or lodge in a cerebral artery, preventing brain regions downstream from receiving perfusing blood flow. The loss of oxygen can rapidly cause brain death in the affected brain regions if the blockage is not soon treated. The cerebral arteries are generally smaller and more tortuous than the corresponding coronary arteries. The required timing and difficult vessel characteristics make reaching and treating the thrombus to prevent brain cell death a most difficult task. The narrow cerebral vessels make placing stents within the brain very difficult using current stents and stent delivery systems. Microcatheters are currently used to infuse drugs into cerebral blood vessels. The microcatheters are typically not greater than about 4 Fr. (1⅓ min.) in outer diameter, currently being generally unsuitable for delivery of cerebral stents.

Stents have been extensively utilized in an attempt to prevent or limit restenosis. Stents are typically tubular devices delivered to the stenosed and dilated site. The stents can be expanded into place against the treated region walls, hopefully preventing restenosis and further narrowing at the stented location. Stents are often formed of metal, commonly stainless steel or Nitinol. The stents can be open walled structures formed from lattice-like cages, spiral wire structures, braided structures, and helically wound and counter-wound structures. Stents can be self-expanding, designed to expand radially when distally advanced from a restraining delivery catheter. Stents can also be balloon-expandable. Balloon-expandable stents can be positioned and then expanded from within using a stent delivery balloon and/or an angioplasty balloon.

A typical stent delivery device includes a stent constrained within an outer delivery sheath extending over the length of the stent. When the device is advanced to the target site, the outer sheath is proximally retracted and/or the stent is distally advanced from within the sheath to the target site. The delivery sheaths may work as intended, but do add bulk to the distal end of the delivery device. In particular, the delivery sheath adds at least one additional layer surrounding the stent. The delivery sheaths are generally cylindrical in nature and extend over the entire length of the stent. The stent can act to reinforce the outer sheath. The delivery sheath and enclosed stent thus act to form a rather rigid composite structure that is not as able to bend and traverse the tortuous vessel regions often found in the human body. The composite structure is thus not as flexible as either the stent or sheath alone would be in traversing these passages.

The added bulk and profile or cross-sectional area of the delivery device can thus act to restrict the use of such stents to larger vessels. In particular, this may leave smaller vessels unreachable and untreatable. Sites requiring treatment disposed on the distal side of a tortuous curve may also be unreachable and untreatable.

In use, some currently available stents and delivery systems also have another limitation. For self-expanding stents, stent placement is often imprecise. The placed or final stent length is related to the final stent diameter that is related to the vessel diameter. Within a vessel, the diameter is not always precisely known, and can vary over the region to be stented. It may be nearly impossible to predict the final stent length before the stent is fully expanded in the vessel.

The difficulty in accurate stent placement can become an issue in stenting a vessel ostium. It is often desirable to place a stent precisely at the ostium of a vessel, especially in coronary and renal vessels. If the stent is positioned too proximal, the stent extends into the trunk line, and can cause flow disturbance. If the stent is positioned too distal, the disease at the ostium is not treated. Self-expanding stent delivery systems typically deploy the stent from distal to proximal, with the distal stent end being advanced distal-most. In particular, a self-expanding stent may be advanced while disposed within a delivery sheath. When the sheath distal end is in position, the sheath can be refracted, allowing the accurately placed stent distal end to expand first. The proximal end of the stent can vary depending on the vessel diameter. In order to accurately place the stent proximal end, the treating physician thus needs to guess at the position to start stent deployment based on the assumed final stent length, so that the proximal end of the stent ends up at the precise ostial location desired.

What would be desirable are devices and methods for delivering stems to target vessel regions that do not require the added bulk of an external restraint or capture sleeve over the stent. Applicants believe that devices and methods not absolutely requiring a delivery sheath over the stent would allow smaller, more tortuous, and more distal vessels to be effectively treated.

SUMMARY OF THE INVENTION

The present invention includes devices and methods for delivering stents to target vessel regions within the body. Methods and devices for delivering everted stents are preferred and disclosed. One stent delivery assembly includes a delivery tube having a stent slidably disposed over the delivery tube distal region, and having the stent distal region everted over the delivery tube distal end, such that the stent distal end is tucked inside of the delivery tube distal end lumen. An elongate release member having a distal element can be slidably disposed within the delivery tube lumen. The release member distal element can be dimensioned relative to the surrounding delivery tube distal end inside diameter so as to form a tight fit between the release member distal element and the surrounding delivery tube. The stent distal region can be held by a friction or interference fit between the release member distal element and surrounding delivery tube walls. The stent is thus everted and reduced in outer diameter at the leading, everted distal end.

In one delivery device, the elongate release member is pulled from the proximal region, thereby proximally urging the release member distal element free of the stent distal end captured between the release member distal element and the surrounding delivery tube distal end. In such embodiments, the release member function may be served by an elongate string or wire having significant strength mainly in tension rather than compression. In another embodiment of the invention, the elongate release member function is served by a shaft having sufficient strength in compression to distally urge the release member distal element by manipulating the release element proximal region, forcing the distal element from the surrounding delivery tube distal end, thereby freeing and unconstraining the stent distal region. In some embodiments, the delivery tube functionality is served by a delivery shaft having only the distal region being tubular in nature. In one such embodiment, the delivery shaft has a distal hoop or annular ring for surrounding and capturing the everted stent distal region within.

In use, the stent can be everted over the delivery tube or shaft, with the stent distal end everted and captured by the elongate release member. The everted stent, delivery shaft or tube, and release member can be advanced distally to a target vessel region to be stented. Once at the target region location, the everted and constrained stem may be freed of the delivery shaft or tube by the release member. The release member may be retracted proximally in some embodiments, and advanced distally in other embodiments, as previously discussed, to release the everted stent. Once released, the stent is free to expand radially and approach the surrounding vessel walls or blockage.

Self-expanding stents can be used in some embodiments of the invention. The stents are preferably biased to radially expand when freed of the constraints of the delivery tube and release member. In other embodiments, balloon expandable stents are used, which can be expanded using inflatable balloon catheters or other stent delivery devices.

Some methods according to the present invention can utilize a guide wire to facilitate advancement of a guide catheter or microcatheter to a location near the vessel region to be stented. The guide wire can be retracted, and the carried everted stent advanced by the release member and guide tube together through the guide catheter or microcatheter to the target region. In one method, the everted stent carried by the delivery tube and release member are advanced distally from the guide catheter to cross the target region, for example, a blood vessel stenosis. In another method, the microcatheter together with the everted stent carried by the delivery tube and release member are advanced through the stenosis or other blockage, followed by proximally retracting the microcatheter, leaving the everted stent to expand against the target region vessel or blockage walls. Once the everted stent is in location, the release member can be activated by advancing or retracting the member to free the everted stent.

Once unconstrained, the stent, for example, a self-expanding stent, may expand to approach the vessel walls or the blockage. In some embodiments, the release member may be advanced distally through the previously placed stent lumen to guarantee a minimal lumen through the stent and/or to act as a guide member for other devices to be passed through the now stented region. In one method, the delivery tube is advanced through the now stented region, which can act to further dilate the stent. In another method, the guide catheter or microcatheter can also be advanced through the now stented region, which can act to further dilate the stent. Thus, a succession of ever increasing diameter devices may be advanced through the stent after stent deployment in some methods. In another method, a balloon catheter is advanced through the now stented region followed by inflation of the balloon and concomitant dilation of the stent.

In another use of the present invention, an everted porous stent carried by a delivery tube can be distally advanced through a thrombosed blood vessel region. A wire mesh or braided stent may be used. The everted stent can be released from the delivery tube to expand against the thrombus. The delivered stent can thus act to stabilize the thrombus. After stenting, the thrombus can be treated by infusing thrombolytic agents near the thrombus, through the walls of the porous stent. The stent can thus act to stabilize the thrombus, preventing large pieces from breaking off and being carried downstream during the thrombolysis.

Some embodiments of the present invention have distally tapered delivery tubes having very small distal end profiles. In these embodiments, the release member distal element may be very small in profile as well. The limit of the distal profile in such devices may approach the lower size limit in gathering, everting, and compressing the distal region of the stent to be delivered. In these and other embodiments, the leading edge of the stent delivery device can be very benign and atraumatic due to the everted stent forming the distal-most leading edge of the device. Many embodiments of the device thus eliminate the absolute need for a delivery sheath or tube disposed about the stent, thereby eliminating one set of tube profiles from the device, making the distal region more flexible, smaller in profile, and able to reach even more distal and smaller diameter vessels which will benefit from treatment.

DETAILED DESCRIPTION OF THE PREFERRED EMBODIMENTS

The following detailed description should be read with reference to the drawings, in which like elements in different drawings are numbered identically. The drawings, which are not necessarily to scale, depict selected embodiments and are not intended to limit the scope of the invention. Several forms of invention have been shown and described, and other forms will now be apparent to those skilled in art. It will be understood that embodiments shown in drawings and described above are merely for illustrative purposes, and are not intended to limit scope of the invention as defined in the claims that follow.

Figure 1:
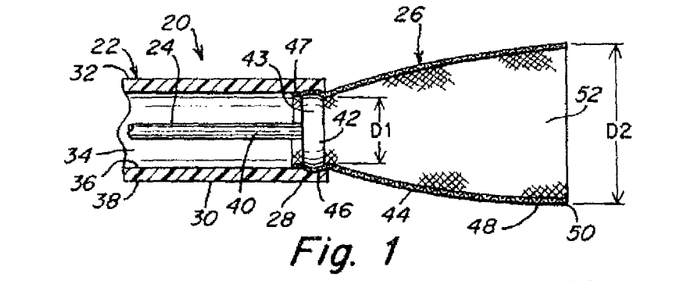
FIG. 1 is a fragmentary, longitudinal, cross-sectional view of a stent delivery assembly including a stent captured between the distal ends of an elongate release member and the surrounding stem delivery tube shown prior to everting the stent proximally over the delivery tube.

FIG. 1 illustrates a stent delivery assembly including a stent delivery device 20, a stent 26, a delivery shaft or tube 22, and an elongate release member 24. Release member 24 can be used to releasably secure or couple stent 26 to delivery shaft or tube 22. Stent 26 is illustrated in a configuration prior to being everted and proximally disposed about delivery tube 22. Delivery tube 22 may be seen to have a distal region 30, a distal end 28, an intermediate region 32, a tube wall 38, a tube wall inner surface 36, and a lumen 34 therethrough. Release member 24 may be seen to have a distal region 40 and a distal end 42 having a distal element 43. In the embodiment illustrated in FIG. 1, release member distal end 42 is dimensioned so as to form an interference fit between stent 26 and delivery tube wall inner surface 36. Delivery tube wall 38 may be seen to be slightly distended in the area of release member distal end 42. Stent 26, described with reference to the everted state, has generally a distal region 46, a distal end 47, an intermediate region 44, a proximal region 48, a proximal end 50, and a lumen 52 therethrough.

Release member 24 may be seen, at distal end 42, to have an outside diameter D1 which closely approximates the inside diameter of delivery tube 22 in the distal region. Stent 26 may be seen gripped between release member distal end 42 and delivery tube 22. Stent 26, in some embodiments, may be biased to expand radially when unconstrained. As illustrated in FIG. 1, stent proximal end 50 has an unconstrained diameter D2 that is substantially larger than the constrained diameter D1. Self-expanding stents are well known to those skilled in the art. Such self-expanding stents may be formed, for example, from Nitinol, which can be heat set to assume a desired shape when unconstrained. Stent 26 in FIG. 1 is illustrated in an intermediate step during assembly. Stent proximal end 50 may be everted and pulled proximally as a sleeve over delivery tube 22. Other methods of assembly are possible. In preferable methods, stent 26 may be heat set in an uneverted shape and disposed as a sleeve over delivery tube distal region 30 in the uneverted state. Stent distal region 46 may then be everted and tucked within delivery tube distal end 28. Release member 24 may then have its proximal end threaded through stent lumen 52 and delivery tube lumen 34 until release member distal end 42 has been proximally retracted within delivery tube distal region 28, firmly capturing stent distal region 46 between the elongate member distal end 42 and the delivery tube distal region 28.

Figure 2:
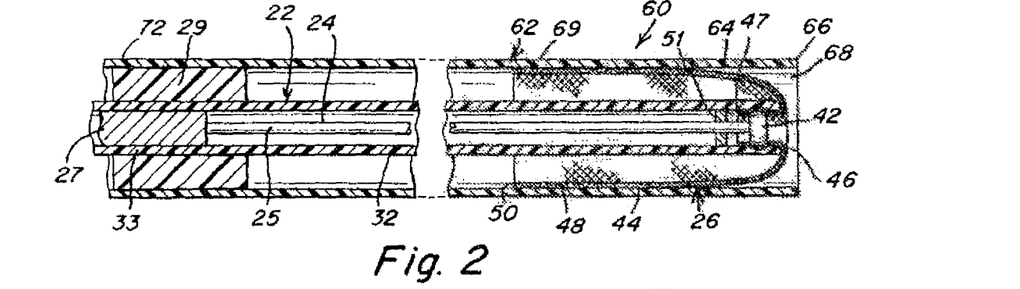
FIG. 2 is a fragmentary, longitudinal, cross-sectional view of the stent delivery assembly of FIG. 1 after the stent has been everted and the device disposed within a guide catheter or microcatheter.

FIG. 2 illustrates stent delivery device 20 further included within a more comprehensive stent delivery assembly 60. Stent delivery assembly 60 includes generally a guide catheter or microcatheter 62 having a distal region 64, an intermediate region 69, a proximal region 72, and a distal end 66 having a lumen 68 therethrough. Release member 24 can have an optional collar 51 disposed about the release member distal region and dimensioned to slidably fit within delivery tube 22. FIG. 2 further illustrates release member 24 having a proximal region 25 coupled to an optional larger diameter proximal end 27 dimensioned so as to form an axially slidable seal between release member proximal end 27 and the surrounding delivery tube proximal region 33. FIG. 2 also illustrates optional annular seal member 29 forming a larger diameter proximal region 33 for the delivery tube 22. Annular element 29 may be seen to form a slidable seal between delivery tube 22 and the surrounding guide catheter or microcatheter 62. FIG. 2 also illustrates that stent 26 can expand outward radially while within guide catheter 62. In particular, stent intermediate region 44, proximal region 48, and proximal end 50 may be seen to have expanded radially to the extent permitted by the surrounding guide catheter 62. The dimensions illustrated for the proximal region of stent delivery assembly 62 and FIG. 2 may vary depending on the embodiment and the intended use. FIG. 2 illustrates only one, non-limiting example of the invention.

Microcatheters are well known devices, commonly used to deliver drugs to cerebral arteries. "Microcatheters", as the term is used herein, is defined to be a tubular catheter having an outside diameter less than about 5 Fr. (1⅔ mm.). Microcatheters used with the present invention preferably have an outside diameter between about 1.5 Fr. (½ mm.) and 4 Fr. (1⅓ mm.), inclusive. Microcatheters preferably have a floppy distal region and tip, the distal region being more pliable and softer than the intermediate and proximal microcatheter regions.

Figure 3:
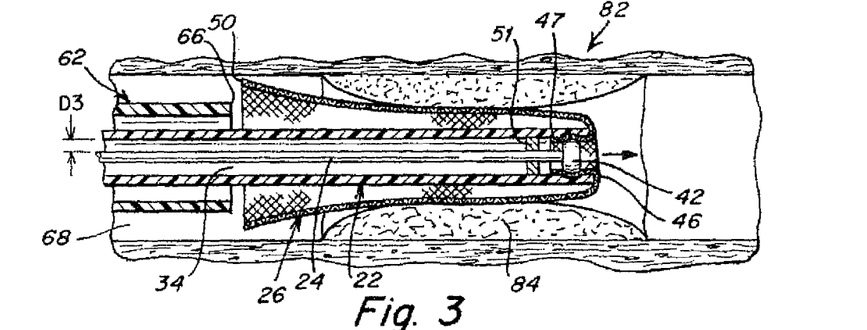
FIG. 3 is a fragmentary, longitudinal, cross-sectional view of the stent delivery assembly of FIG. 2 after the microcatheter has been advanced proximal of a blockage and the captured, everted stent carried further distally by the release member and delivery tube.

FIG. 3 illustrates one use of assembly 60 in a body conduit or vessel 82 having a target region 80 at least partially occluded by a blockage 84. Blockage 84 can at least partially block vessel 82, thereby reducing the effective size of vessel lumen 86. Blockage 84 represents any of a number of blockages, including, but not limited to plaque, thrombus, and a stenosed vessel region generally.

In one method according to the present invention, a guidewire is advanced distally through the vessel until the guidewire distal tip is across or proximally near vessel target region 80. Guide catheter or microcatheter 62 can then be advanced over the placed guidewire until microcatheter distal end 66 is disposed proximal of blockage 84. In some methods, the guidewire is now retracted proximally from microcatheter 62.

With microcatheter 62 in place, stent delivery device 20 may be advanced through microcatheter lumen 68 to a position within microcatheter 60 proximal of vessel target region 80. As may be seen from inspection of FIG. 3, stent 26 is everted over the distal end of delivery tube 22 and releasably secured to delivery tube 22 with elongate release member distal end 42. In the embodiment illustrated, stent 26 is a self-expanding stent, with proximal end 50 having a larger outside diameter than constrained distal end 47.

With release member 24, delivery tube 22, and everted stent 26 in position, the release member, the delivery tube, and the captured, constrained and everted stent 26 may be distally advanced across the target site 80 having blockage 84. In some methods, the advancing of release member, delivery tube, and everted stent is accomplished while leaving guide catheter or microcatheter 62 positioned proximal of the vessel target site. In other methods, guide catheter or microcatheter 62 is advanced across target vessel region 80. In one method, microcatheter 62, everted stent 26, delivery tube 22, and release member 24 are all advanced together across target region 80. In this method, after microcatheter 62 and constrained, everted stent 26 are across target vessel region 80, microcatheter 62 can be proximally retracted, exposing the stent.

As may be seen from inspection of FIG. 3, stent 26 is still releasably secured to delivery tube 22 and may be further advanced distally. In some uses of the invention, a microcatheter such as microcatheter 62 may be used to advance the releasably secured stent and delivery tube only so far as the microcatheter can reach, followed by the distal exit of the everted stent from the microcatheter to attain even greater distal reach for the stent. FIG. 3 also illustrates that stent 26 can be axially elongated as the stent is pulled through narrow passages, which can reduce the stent profile while the stent is being pulled.

Once everted stent 26 is at the desired location, the stent can be released from delivery tube 22. In one example of the invention, release member 24 is urged proximally, thereby pulling the release member distal end proximally until release member distal end 42 is disposed proximally of everted stent distal end 47. Stent 26 may then expand further radially to embrace the surrounding vessel target region 80. In another example of the invention, elongate release member 24 can be distally urged, thereby forcing release member distal end 42 distally from delivery tube 22, thereby releasing stent 26 from delivery tube 22. In embodiments having optional collar 51, the collar can be used to help push out the stent after release. Both distal and proximal movement of release member 24 can be accomplished by manipulating the proximally accessible portion of the release member. Stent 26 is then free to radially expand and retain its previous, non-everted shape.

It may be seen from inspection of FIG. 3 that everted stent 26 has a smaller distal profile than proximal profile, allowing easier entry into narrow target sites. In some embodiments of the invention, delivery tube 22 has a tapered distal tip, such that the profile of the distal end of delivery tube 22 is smaller than the profile of delivery tube 22 in an intermediate or proximal location. FIG. 3 also illustrates that the everted distal region 46 of stent 26 forms a rather atraumatic tip, relative to many other distal delivery devices and, in most embodiments, more benign than the delivery tube distal end 28. Due in part to the self-expanding nature of the stent illustrated in FIG. 3, distally urging the half released, half secured stent forms a proximally widening shape that can act to initially penetrate, then dilate a blocked vessel region, prior to totally releasing the stent.

The distance between release member 24 and delivery tube 22 is indicated at D3 in FIG. 3. In some embodiments, the proximal and intermediate regions of delivery tube 22 have a very tight fit between release member 24 and delivery tube 22. A close tolerance between the release member and the delivery tube can provide columnar support for advancing release member 24. Such close tolerance can also provide strength and stability when the elongate release member 24 is retracted proximally to release stent 26, in embodiments calling for such retraction.

Figure 4:
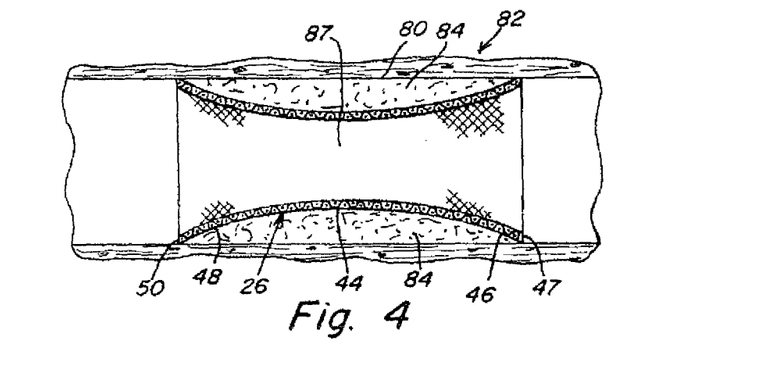
FIG. 4 is a fragmentary, longitudinal, cross-sectional view of the assembly of FIG. 3 after the stent has been released and expanded within the target vessel region.

FIG. 4 illustrates vessel target region 80 after stent 26 has been expanded to create and stabilize an expanded or dilated flow channel 87 through vessel 82. Stent proximal region 48 and distal region 46 may be seen to have expanded radially against blockage 84. Stent 26 is preferably radially expanded outwardly against the vessel walls and/or blockage once released by release member 24. In one method, stent 26 is biased to radially expand outwardly, once unconstrained. Some self-expanding stents useful with the present invention are formed of Nitinol. Stents may be heat-set to radially expand and assume the heat-set diameter once released in some methods.

In one method according to the invention, after stent 26 has been allowed to expand radially, this process may be assisted using parts of the device previously described. In embodiments where the release rod has sufficient strength in compression to be pushed, release member 24 may be advanced distally through deployed stent 26 to ensure that an initial clear flow passage exists through stent 26. Elongate release member 24 may be followed by distally advancing delivery tube 22 through deployed stent 26. In other methods, guide catheter or microcatheter 62 may be advanced through deployed stent 26, to further widen the already stented passage. These methods may also be employed to assist with eversion of the distal end of the released but incompletely deployed stent. In some methods, the delivery tube and release member may be retracted proximally, and an inflatable balloon catheter advanced to the now stented vessel site to further dilate the deployed stent by inflating the inflatable balloon disposed in the balloon catheter distal region.

FIG. 3 illustrates only one embodiment of the invention, which is not necessarily drawn to scale. In particular, in some embodiments, the distal region of delivery tube 22 can be significantly smaller in profile. In one embodiment, release member 24 has distal end 42 being substantially smaller in profile than that illustrated in FIG. 3. In one embodiment, distal end 42 is tapered distally or proximally to facilitate the frictional fit between the stent and the delivery catheter. The inside of the delivery catheter distal region and/or outside of the release member distal end 42 can be coated with a compressible, tacky, flowable, or high friction material to augment the security of reversible stent engagement. In one device, release member distal end 42 is only slightly larger in profile than the intermediate portion of release member 24. In one embodiment, release member 24 has strength substantially only in tension rather than compression, and acts as a string. This string or wire can be very small in profile, and can be coupled to a very small release member distal element. In one embodiment, elongate release member 24 is a fine gauge wire, metallic or polymeric, coupled to a small distal plug. Delivery tube distal end 28 may also be much smaller and significantly distally tapered relative to that illustrated in FIG. 3. Delivery tube distal end 28 may also be reinforced against diametric enlargement by incorporation of a strong circular loop or band within or outside of the wall of the delivery tube distal end. Preferably the loop or band is metallic and more preferably radiopaque so as to facilitate visualization under fluoroscopy.

Inspection of FIG. 3 indicates that the lower limit on the transverse cross-sectional size or profile of the stent delivery assembly may be limited by the profile of the everted stent 26. In one embodiment of the invention, elongate release member 24 is effectively a thin wire or string terminating distally in a plug or ball shape only slightly larger in profile than the wire or string. Delivery tube 22 may be significantly distally tapered such that the inside diameter of the delivery tube distal end approaches the outer diameter of the release member distal end or plug 42. The stent may thus be everted and the stent distal region tightly bunched or gathered together between the small distal ball or plug and the surrounding, tapered, distal end of the delivery tube. While the release member and delivery tube occupy space, it may be seen that the absolute lower limit of the cross-sectional profile in some embodiments may be ultimately bounded by the lower size limit in releasably compressing the stent distal end.

Figure 5A:
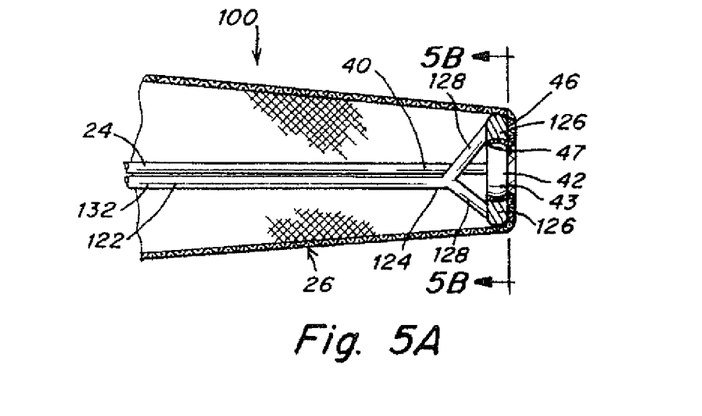
FIG. 5A is a fragmentary, longitudinal, cross-sectional view of an alternate embodiment of the invention where the delivery tube is a delivery shaft having a distal tube or ring.
Figure 5B:
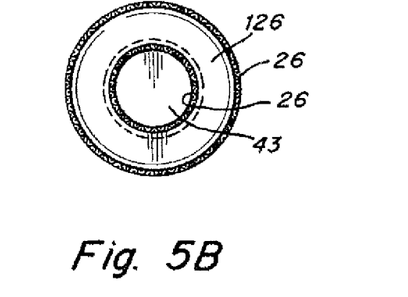
FIG. 5B is a wafer view taken through 5B of FIG. 5A, illustrating the fit between the release member distal end, everted stent, and delivery shaft distal end.

FIG. 5A illustrates another embodiment of the invention. The stent delivery assembly 100 illustrated in FIG. 5A can be similar to that of assembly 20 as illustrated in FIGS. 1 and 2. Delivery assembly 100 may be seen to have an everted stent 26 and an elongate release member 24 as previously discussed. Assembly 100 has a delivery shaft 122 rather than a delivery tube. Delivery shaft 122 has an intermediate region 132 extending to a distal region 124. Distal region 124 includes support struts 128 extending distally and radially outward to support a short tube section or annular ring 126. In some embodiments, annular tube or ring 126 may be significantly longer than that illustrated in FIG. 5A, which is not necessarily to scale. The distal region of delivery shaft 122 may thus form a delivery tube in the many respects previously discussed. Stent 26 may be seen to be everted over distal annular ring or hoop 126 and held in place by a tight, interference fit between release member distal element 43 and annular ring 126. As may be seen from inspection of FIG. 5A, everted stent 26 may be released from the assembly 100 by proximally retracting release member 24 or distally extending release member 24, depending on the embodiment and the properties of the release member shaft forming release member 24. FIG. 5B illustrates a transverse cross-sectional view of the assembly 100 of FIG. 5A, showing release end element 43 disposed within one layer of stent 26 which is in turn disposed within annular ring 126 which has a second layer of stent 26 disposed to the outside.

Figure 5C:
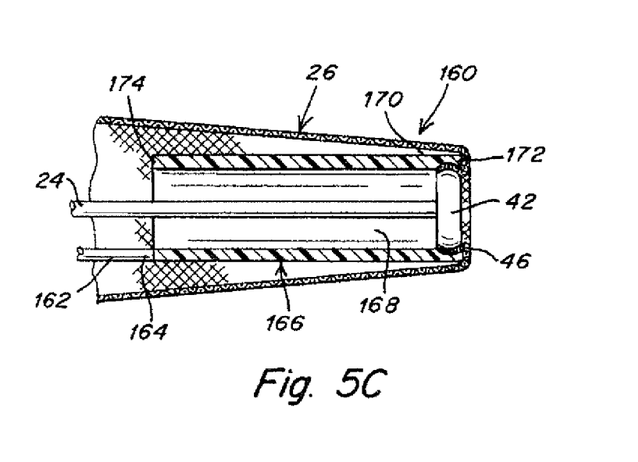
FIG. 5C is a fragmentary, longitudinal, cross-sectional view of another embodiment of the invention, where the delivery tube has a tubular distal region and coupled to a proximal shaft.

FIG. 5C illustrates another stent delivery assembly 160, somewhat similar to that of delivery assembly 100 of FIG. 5A and having the same reference numerals for similar elements. Assembly 160 includes elongate release member 24 and stent 26 as previously discussed. The delivery device includes a distal tube 166 coupled to a proximal elongate member or shaft 162. Tube 166 includes a proximal end 174, a distal region 170, a distal end 172, and a lumen 168 extending through the tube. Proximal shaft 162 can be coupled to tube 160 at a shaft distal region 164. Proximal shaft 162 can extend distally along or within tube 166 in some embodiments. Tube 166 may be slit to accommodate proximal shaft 162.

Stents that may be used with the present invention include self-expanding and balloon expandable stents, well known to those in the cardiovascular arts. Stents may be formed from many of the well known stent materials, including Nitinol, stainless steel, and polymers. The stents may be braided, knit, meshed, formed of non-woven wires, helically wound and helically counterwound. Stents according to the present invention are preferably porous, wire, braided stents, with various embodiments having an average pore or inter-wire opening size of at least about 20 microns in one embodiment, and at least 50 microns in another embodiment. In a preferred embodiment the stent ends are coated with flexible adherent material to prevent unraveling of, for example, braided stents. Alternatively, the stent strands can be welded or otherwise fastened to one another to prevent unraveling during eversion.

In one use of the invention, the everted stent may be used to stabilize a blockage such as a thrombus, while providing a perfusing path through the dilated thrombus. In another use, the stent may be positioned across a stenosed blood vessel region, and the region treated with a restenosis inhibiting agent. The restenosis inhibiting agent can be infused through the porous stent wall or reside on the stent itself and release into the vessel wall. FIGS. 3 and 4 may be used to visualize blockage 84 being formed primarily of thrombus, with stent 26 being put in place to primarily stabilize the thrombus and to provide oxygenating blood flow to downstream brain regions, preventing brain cell death. Small distal profile catheters as previously discussed and as illustrated in FIG. 3 may thus be used to advance an everted stent across a thrombus and deploy the stent. The stent, which can be either self-expanding or expandable from within using a stent placement device, can then expand against the vessel walls and/or blockage. In some methods, an infusion catheter is advanced to within vessel site 80, and thrombolytic agents infused through the porous stent wall. Various therapeutic agents may be applied in this way. A non-limiting list of such therapeutic agents includes thrombolytic agents, anticoagulants, anti-platelet agents, and tissue plasminogen activator. In a similar way, stents according to the present invention can be used to treat an area stenosed because of arteriosclerosis.

The present invention can be used to accurately position the stent proximal end. The stent proximal end may be positioned accurately relative to a vessel ostium. The stent can be positioned near the proximal end of a stenosis located near or at an ostium. The everted stent can be advanced as previously discussed, until the proximal end is positioned at the desired location. The stent proximal end can be allowed to radially expand against the vessel walls. In some methods, the stent can be advanced further distally until the expanded proximal end is at the desired position. The stent placement may be followed using fluoroscopy. This desired position may be exactly at the ostium beginning, slightly within the ostium, or extending slightly from the ostium. The stent distal region can be released and allowed to expand. In this way, the stent proximal end can be positioned accurately relative to the ostium.

In one embodiment of the invention, the elongate release member has a length of between about 100 cm. and 200 cm. In one embodiment, the outer diameter of the release member distal element is less than 2 mm. In various embodiments, the release member may be formed from stainless steel, Nitinol, polyimide, reinforced polymer, or PEEK and the like.

The delivery tube or shaft in some embodiments has a length of between about 75 cm. and 175 cm. The delivery tube can have an outside diameter of between about 6 Fr. and 1 Fr. In various embodiments of the invention, the distal region of the delivery tube may be distally tapered. In some embodiments, the cross-sectional outer diameter of the delivery tube distal end is less than about 6 Fr. Delivery tubes can be made from flexible polymers such as PEBAX, nylon, polyester, polyurethane, polyethylene, FEP, Teflon, silicone, and the like, with or without reinforcement by metallic or polymeric elements. Microcatheters are well known to those skilled in the art and any suitably sized guide catheter or microcatheter may be used in combination with the present invention, preferably about 3 Fr. or 4 Fr. in outer diameter. Some exemplary sized catheters that can be used with the present invention are between about 75 cm. and 175 cm. in length. Guide or microcatheters useful in conjunction with the present invention may be formed from Nylon, PEBAX, polyurethane, and the like. Guide catheters can be reinforced with metallic braids, with microcatheters preferably having very flexible distal end regions. The catheters can have a distal outer diameter of less than about 8 Fr. for guides and 4 Fr. for microcatheters.

The invention claimed is:

1. A stent delivery assembly comprising:
   a microcatheter having a distal region, a proximal region, and a lumen that extends from the proximal region through the distal region;
   a delivery tube having a lumen and a distal end, the delivery tube extending within the microcatheter lumen;
   a stent having a first end, a second end, an intermediate region disposed between the first end and the second end, and a lumen extending from the first end to the second end, the first end being (i) disposed within the delivery tube lumen and (ii) constrained by the delivery tube from radially expanding beyond a delivery tube lumen diameter, the second end being (i) disposed outside of the delivery tube distal end and (ii) substantially radially unconstrained by the delivery tube to expand beyond the delivery tube lumen diameter; and an elongate release member having a distal portion and extending within the delivery tube lumen and the stent lumen, the distal portion being moveable between a first position, in which the distal portion and the delivery tube collectively engage the stent first end to fix the stent first end relative to the delivery tube lumen, and a second position, in which the distal portion is moved beyond the delivery tube distal end to release the stent first end.

2. The assembly of claim 1, wherein the stent is configured to radially expand when radially unrestrained from the delivery tube.

3. The assembly of claim 1, wherein in the first position, the distal portion and the delivery tube lumen collectively engage the stent first end to fix the stent first end relative to the delivery tube lumen.

4. The assembly of claim 1, wherein the release member distal portion presses the stent first end radially outwardly against the delivery tube.

5. The assembly of claim 1, wherein the release member distal portion has a profile dimensioned to form a friction fit between the stent first end and the delivery tube distal end, the stent first end being disposed about the distal portion, and the delivery tube distal end being disposed about the stent first end.

6. The assembly of claim 5, wherein the release member is configured to advance the distal portion thereof distally from the delivery tube distal end, thereby releasing the stent from the delivery tube.

7. The assembly of claim 5, wherein the release member is configured to retract the distal portion proximally relative to the stent first end, thereby releasing the stent from the delivery tube.

8. The assembly of claim 7, wherein the release member is configured to retract the distal portion proximally into the delivery tube, thereby releasing the stent from the delivery tube.

9. The assembly of claim 1, wherein the microcatheter distal region is disposed over the delivery tube distal region.

10. The assembly of claim 1, wherein the stent first end is captured between the release member distal portion and the delivery tube.

11. The assembly of claim 10, wherein the stent first end is captured radially between the release member distal region and the delivery tube.

12. A method for delivering a tubular stent to a target vessel region, the method comprising the steps of:
providing a stent having a first end and a second end;
providing a microcatheter having a distal region, a proximal region, and a lumen that extends from the proximal region through the distal region;
providing a delivery tube having a lumen and a distal end, the delivery tube extending within the microcatheter lumen, wherein the stent first end is disposed within the delivery tube lumen such that the delivery tube constrains the stent first end from radially expanding, and the stent second end is disposed outside of the delivery tube distal end such that the stent second end is substantially radially unconstrained by the delivery tube;
providing an elongate release member having a distal portion extending within the delivery tube lumen, the distal portion having a first position, in which the distal portion and the delivery tube engage the stent first end to fix the stent first end relative to the delivery tube distal end;
advancing the stent, the microcatheter, the delivery tube, and the release member distally to a location near the target vessel region; and
moving the release member to a second position to release the stent first end.

13. The method of claim 12, wherein the moving step comprises proximally retracting the release member relative to the first position.

14. The method of claim 12, wherein the moving step comprises distally advancing the release member relative to the first position.

15. The method of claim 12, wherein in the first position, the distal portion and the delivery tube lumen collectively engage the stent first end to fix the stent first end relative to the delivery tube lumen.

16. The method of claim 12, wherein in the first position, the distal portion presses the stent first end radially outwardly against the delivery tube.

17. The method of claim 12, further comprising radially expanding the stent after the moving step.

18. The method of claim 17, wherein the radially expanding step includes allowing the stent first end to radially expand upon release, wherein the stent first end is configured to expand radially when radially unrestrained from the delivery tube distal end.

19. The method of claim 12, further comprising distally advancing the stent, delivery tube, and release member within the microcatheter; and advancing the stent, delivery tube, and release member distally from the microcatheter distal end across the target vessel region.

20. The method of claim 12, further comprising distally advancing the stent, delivery tube, and release member within the microcatheter; advancing the microcatheter, stent, delivery tube, and release member distally across the target vessel region; proximally retracting the microcatheter from the target vessel region to release the stent second end into contact with the target vessel region; and manipulating the release member to release the stent first end into contact with the target vessel region.

21. A stent delivery assembly, the assembly comprising:
a microcatheter having a distal region, a proximal region, and a lumen that extends from the proximal region through the distal region;
a delivery tube having a lumen, a lumen diameter, and a distal end, the delivery tube extending within the microcatheter lumen;
a release member positioned within the lumen of the delivery tube; and
a stent having a first end and a second end, the first end being disposed within the delivery tube distal end and grasped between the delivery tube and the release member, the second end being disposed outside of the delivery tube distal end and substantially radially unconstrained by the delivery tube to expand to a diameter greater than the delivery tube lumen diameter.

22. The assembly of claim 21, wherein the release member has an outer surface, the stent first end being pressed between the outer surface and the delivery tube.

23. The assembly of claim 22, wherein in the first position, the distal portion presses the stent first end radially outwardly against the delivery tube.

24. The assembly of claim 21, further comprising a catheter positioned over at least a portion of the delivery tube.

25. The assembly of claim 21, wherein the release member is configured to be advanced distally from the delivery tube distal end, thereby releasing the stent from the delivery tube.

26. The assembly of claim 21, wherein the release member is configured to be retracted proximally relative to the stent body first end, thereby releasing the stent from the delivery tube.

\* \* \* \* \*